United States Patent [19]
DeLuca

[11] Patent Number: 5,321,018
[45] Date of Patent: Jun. 14, 1994

[54] USE OF 1α-HYDROXYLATED-19-NOR-VITAMIN D COMPOUNDS TO TREAT PSORIASIS

[75] Inventor: Hector F. DeLuca, Deerfield, Wis.

[73] Assignee: Wisconsin Alumni Research Foundation, Madison, Wis.

[21] Appl. No.: 987,258

[22] Filed: Nov. 20, 1992

Related U.S. Application Data

[63] Continuation of Ser. No. 579,935, Sep. 7, 1990, abandoned, which is a continuation-in-part of Ser. No. 481,354, Feb. 16, 1990, Pat. No. 5,237,110, which is a continuation-in-part of Ser. No. 321,030, Mar. 9, 1989, abandoned.

[51] Int. Cl.$^5$ .................. A61K 31/595; A61K 31/56
[52] U.S. Cl. .................................. 514/167; 514/168; 514/169; 514/171; 552/653
[58] Field of Search ............... 514/167, 168, 169, 171; 552/653

[56] References Cited

U.S. PATENT DOCUMENTS

| | | | |
|---|---|---|---|
| 4,195,027 | 3/1980 | DeLuca et al. | 552/653 |
| 4,237,125 | 12/1980 | Bannai et al. | 514/167 |
| 4,610,978 | 9/1986 | Dikstein et al. | 514/46 |
| 4,728,643 | 3/1988 | Holick et al. | 514/167 |

Primary Examiner—Marianne M. Cintins
Assistant Examiner—T. J. Griares
Attorney, Agent, or Firm—Andrus, Sceales, Starke & Sawall

[57] ABSTRACT

A novel use for 1α-hydroxylated-19-nor-vitamin D compounds to treat psoriasis inasmuch as these compounds when administered to humans are converted to a metabolite, such as a 1α,25-dihydroxylated compound, which metabolite in vitro will cause differentiation in a human cell line.

53 Claims, No Drawings

USE OF 1α-HYDROXYLATED-19-NOR-VITAMIN D COMPOUNDS TO TREAT PSORIASIS

This invention was made with United States Government support awarded by the National Institute of Health (NIH), Grant # DK-14881. The United States Government has certain rights in this invention.

This application is a continuation application of Ser. No. 07/579,935, filed Sep. 7, 1990, now abandoned, which in turn is a continuation in part application of application Ser. No. 07/481,354 filed Feb. 16, 1990, now U.S. Pat. No. 5,237,110, which in turn is a continuation-in-part application of application Ser. No. 07/321,030 filed Mar. 9, 1989, abandoned.

BACKGROUND OF THE INVENTION

The present invention relates to vitamin D compounds, and more particularly to the use of 1α-hydroxylated-19-nor-vitamin D compounds to treat psoriasis.

The D vitamins are very important agents for the control of calcium and phosphate metabolism in animals and humans, and have long been used as dietary supplements and in clinical practice to assure proper bone growth and development. It is now known that the in vivo activity of these vitamins, specifically of vitamin $D_2$ and $D_3$, is dependent on metabolism to hydroxylated forms. Thus, vitamin $D_3$ undergoes two successive hydroxylation reactions in vivo, leading first to 25-hydroxyvitamin $D_3$ and then to 1,25-dihydroxyvitamin $D_3$ and the latter is indeed thought to be the compound responsible for the well-known beneficial effects of vitamin $D_3$. Likewise, vitamin $D_2$, which is commonly used as a dietary supplement, undergoes an analogous hydroxylation sequence to its active forms, being first converted to 25-hydroxyvitamin $D_2$ (25—OH—$D_2$) and then to 1,25-dihydroxyvitamin $D_2$ (1,25—(OH)$_2D_2$). These facts are well established and well known in the art (see, for example, Suda et al. Biochemistry 8, 3515 (1969) and Jones et al. Biochemistry 14, 1250 (1975)).

Hollick, U.S. Pat. No. 4,728,643 discloses a method of treating psoriasis with vitamin D compounds which in vitro cause cell differentiation. However 1α-hydroxylated vitamin D compounds, i.e. those compounds having only a hydroxyl group at the carbon 1 position and initially lacking a hydroxyl group at the carbon 24 or 25 positions, are relatively inactive in causing cell differentiation in vitro. Additionally, it is also well known that 1α-hydroxylated compounds are rapidly converted in vivo to 1α,25-dihydroxy compounds, e.g. 1α-hydroxyvitamin $D_3$ to 1α,25-dihydroxy-vitamin $D_3$, or if the 25 carbon position is blocked to 1α,24-dihydroxy compounds. Hollick et al, *Science*, Vol. 190, pages 576-578 (1975) and Hollick et al, *J. of Clinical Endocrinology & Metabolism, Vol.* 44, pages 595-598 (1977). For example, in PCT patent application number PCT/DK89/00079 filed Apr. 7, 1989 and published Nov. 2, 1989 under number WO89/10351 there is disclosed numerous side chain homologated vitamin D compounds lacking the hydroxyl group at the carbon 25 position in the side chain. It is disclosed therein that such compounds are converted in vivo to active compounds having a hydroxyl group at the carbon 25 position by enzymatic hydroxylation, and may thus be used for the treatment of psoriasis. Thus, the human body can rapidly convert relatively inactive 1α-hydroxylated vitamin D compounds to metabolites highly active in causing cell differentiation. There has, however, been a failure in the art to recognize the ability of 1α-hydroxylated-19-nor-vitamin D compounds to treat malignancies such as psoriasis.

SUMMARY OF THE INVENTION

Compositions containing one or more 1α-hydroxylated-19-nor-vitamin D compounds which compounds when administered to humans are converted to a metabolite, which metabolite in vitro has cell differentiation activity, together with a suitable carrier useful in the treatment of psoriasis are described. The treatment may be topical, oral or parenteral. Methods of employing the compositions are also disclosed. The compounds are present in the composition in an amount from about 0.01 μg/gm to about 100 μg/gm of the composition, and may be administered orally or parenterally in dosages of from about 0.01 μg/day to about 100 μg/day.

The compounds disclosed herein unexpectedly provide highly effective treatments for psoriasis without producing unwanted systemic or local side effects. Accordingly, one aspect of the invention comprises a method of treating psoriasis which comprises administering to a patient an effective amount of a 1α-hydroxylated-19-nor-vitamin D compound which compound upon administration to humans is converted to a metabolite and said metabolite in vitro will cause differentiation of promelocytes to monocytes in a cell line selected from the group consisting of a U937 cell line, an HL60 cell line and a M1 cell line.

DETAILED DESCRIPTION OF THE INVENTION

The vitamin D compounds useful in the compositions of the present invention and for the treatment of psoriasis and other malignancies are those which are solely 1α-hydroxylated, i.e. those that do not initially have a hydroxyl group at the 24 or 25 carbon position in the side chain. Such 1α-hydroxylated compounds are readily converted to 1α, 25-dihydroxy or 1α,24-dihydroxy compounds in vivo. These dihydroxy compounds are highly potent in inducing cellular differentiation, and the preferred compounds are those which induce cellular differentiation with minimal or no effect on either intestinal calcium absorption or bone calcium mobilization. Accordingly, specific preferred examples of vitamin D compounds defined by the above functions are those selected from the group consisting of 1α-hydroxy-19-nor-vitamin D compounds.

The 1α-19-nor-vitamin D compounds referred to herein are a class of 1α-hydroxylated vitamin D compounds in which the ring A exocyclic methylene group (carbon 19) typical of all vitamin D systems has been removed and replaced by two hydrogen atoms. Structurally these novel analogs are characterized by the general formula II shown below:

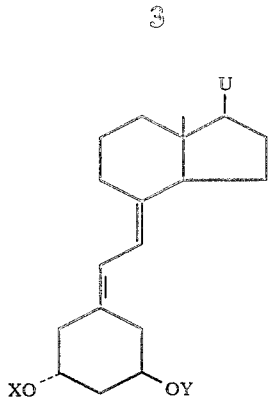

where X and Y are each selected from the group consisting of hydrogen, acyl, alkylsilyl and alkoxyalkyl, and where the group U represents any of the typical side chains known for vitamin D compounds that are not hydroxylated at the carbon 25 position in the side chain. Thus, U may represent the following side chain:

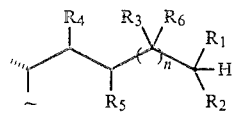

wherein $R_1$ and $R_2$ are each selected from the group consisting of alkyl, hydroxyalkyl and fluoroalkyl, deuteroalkyl or, when taken together represent the group—$(CH_2)_m$—where m is an integer having a value of from 2 to 5, $R_3$ is selected from the group consisting of hydrogen, deuterium, hydroxy, fluorine, O-acyl, alkyl, hydroxyalkyl and fluoroalkyl, $R_6$ is selected from the group consisting of hydrogen, deuterium, fluorine, alkyl, hydroxyalkyl and fluoroalkyl, or, $R_3$ and $R_6$ taken together represent double-bonded oxygen or double-bonded carbon, $R_4$ and $R_5$ are each selected from the group consisting of hydrogen, deuterium, hydroxy, O-acyl, fluorine and alkyl, or, $R_4$ and $R_6$ taken together form a carbon-carbon double bond or a carbon-carbon triple bond, and wherein n is an integer having a value of from 1 to 5, and wherein the carbon at any one of positions 20, 22, or 23 in the side chain may be replaced by an O, S, or N atom.

Specific important examples of side chains for the 19-nor compounds are the structures represented by formulas (a), (b), (c), (d) and (e) below, i.e. the side chain as it occurs in 25-hydroxyvitamin $D_3$ (a); vitamin $D_3$ (b); 25-hydroxyvitamin $D_2$ (c); vitamin $D_2$ (d); and the C-24-epimer of 25-hydroxyvitamin $D_2$ (e).

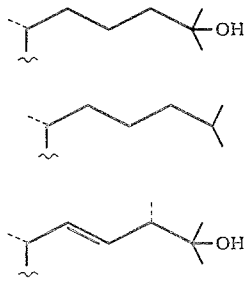

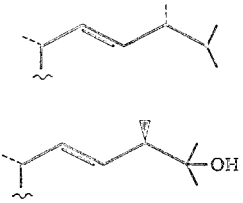

It should be noted that structures (a), (c) and (e) shown above are examples of three 19-nor compounds after each has been metabolized in vivo to 1,25-dihydroxy compounds.

As used in the description, and in the claims, the term "hydroxy-protecting group" refers to any group commonly used for the protection of hydroxy functions during subsequent reactions, including, for example, acyl or alkylsilyl groups such as trimethylsilyl, triethylsilyl, t-butyldimethylsilyl and analogous alkylated silyl radicals, or alkoxyalkyl groups such as methoxymethyl, ethoxymethyl, methoxyethoxymethyl, tetrahydrofuranyl or tetrahydropyranyl. A "protected-hydroxy" is a hydroxy function derivatized by one of the above hydroxy-protecting groupings. "Alkyl" represents a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl", "fluoroalkyl" and "duteroalkyl" refer to such an alkyl radical substituted by one or more hydroxy or fluoro or deuterium groups respectively. An acyl group is an alkanoyl group of 1 to 6 carbons in all its isomeric forms, or an aroyl group, such as benzoyl, or halo-, nitro- or alkyl-substituted benzoyl groups, or a dicarboxylic acyl group such as oxalyl, malonyl, succinoyl, glutaroyl, or adipoyl. The term "aryl" signifies a phenyl-, or an alkyl-, nitro- or halo-substituted phenyl group.

It should be noted in this description that the term "24-dihomo" refers to the addition of two methylene groups at the carbon 24 position in the side chain. Likewise, the term "trihomo" refers to the addition of three methylene groups. Also, the term "26,27-dimethyl" refers to the addition of a methyl group at the carbon 26 and 27 positions so that for example $R_1$ and $R_2$ are ethyl groups. Likewise, the term "26,27-diethyl" refers to the addition of an ethyl group at the 26 and 27 positions so that $R_1$ and $R_2$ are propyl groups.

Specific and preferred examples of these 1α-hydroxylated compounds when the side chain is unsaturated (i.e. $R_4$ and $R_5$ represent a double bond) are: 24-dihomo-1α-hydroxy-19-nor-22-dehydrovitamin $D_3$, i.e. the compound shown above, where X and Y are hydrogen, n equals 3, and $R_1$ and $R_2$ are each a methyl group; 26,27-dimethyl-24-dihomo-1α-hydroxy-19-nor-22-dehydrovitamin $D_3$, i.e. the compound shown above where X and Y are hydrogen, n equals 3, and $R_1$ and $R_2$ are each an ethyl group; 24-trihomo-1α-hydroxy-19-nor-22-dehydrovitamin $D_3$, i.e. the compound having the structure shown above, where X and Y are hydrogen, n equals 4, and $R_1$ and $R_2$ are each a methyl group; 26,27-dimethyl-24-trihomo-1α-hydroxy-19-nor-22-dehydrovitamin $D_3$, i.e. the compound shown above where X and Y are hydrogen, n equals 4, and $R_1$ and $R_2$ are each an ethyl group; 26,27-diethyl-24-dihomo-1α-hydroxy-19-nor-22-dehydrovitamin $D_3$, i.e. the compound shown above where X and Y are hydrogen, n equals 3, and $R_1$ and $R_2$ are each a propyl group; 26,27-diethyl-24-trihomo-1α-hydroxy-19-nor-22-dehydrovitamin $D_3$, i.e. the compound shown above where X and Y are hydrogen, n equals 4, and $R_1$ and $R_2$ are each a propyl group, 26,27-dipropyl-24-dihomo-1α-hydroxy-19-nor-22-dehydrovitamin $D_3$, i.e. the compound shown above where X and Y are hydrogen, n equals 3, and $R_1$ and $R_2$ are each a butyl group; and 26,27-dipropyl-24-trihomo-1α-hydroxy-19-nor-22-dehydrovitamin $D_3$, i.e. the compound shown above where X and Y are hydrogen, n equals 4, and $R_1$ and $R_2$ are each a butyl group.

Specific and preferred examples of these compounds when the side chain is saturated (i.e. $R_4$ and $R_5$ each represent hydrogen) are: 24-dihomo-1α-hydroxy-19-nor-vitamin $D_3$, i.e. the compound shown above, where X and Y are hydrogen, n equals 3, and $R_1$ and $R_2$ are each a methyl group; 26,27-dimethyl-24-dihomo-1α-hydroxy-19-nor-vitamin $D_3$, i.e. the compound shown above where X and Y are hydrogen, n equals 3, and $R_1$ and $R_2$ are each an ethyl group; 24-trihomo-1α-hydroxy-19-nor-vitamin $D_3$, i.e. the compound having the structure shown above, where X and Y are hydrogen, n equals 4, and $R_1$ and $R_2$ are each a methyl group; 26,27-dimethyl-24-trihomo-1α-hydroxy-19-nor-vitamin $D_3$, the compound shown above where X and Y are hydrogen, n equals 4, and $R_1$ and $R_2$ are each an ethyl group; 26,27-diethyl-24-dihomo-1α-hydroxy-19-nor-vitamin $D_3$, i.e. the compound shown above where X and Y are hydrogen, n equals 3, and $R_1$ and $R_2$ are each a propyl group; 26,27-diethyl-24-trihomo-1α-hydroxy-19-nor-vitamin $D_3$, i.e. the compound shown above where X and Y are hydrogen, n equals 4, and $R_1$ and $R_2$ are each a propyl group; 26,27-dipropyl-24-dihomo-1α-hydroxy-19-nor-vitamin $D_3$, i.e. the compound shown above where X and Y are hydrogen, n equals 3, and $R_1$ and $R_2$ are each a butyl group; and 26,27-dipropyl-24-trihomo-1α-hydroxy-19-nor-vitamin $D_3$, i.e. the compound shown above where X and Y are hydrogen, n equals 4, and $R_1$ and $R_2$ are each a butyl group.

The preparation of 1α-hydroxy-19-nor-vitamin D compounds having the basic structure shown above in formula II can be accomplished by a common general method, using known vitamin D compounds as starting materials. Suitable starting materials are, for example, the vitamin D compounds of the general structure IV:

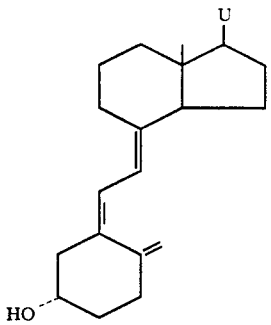

IV where U is any of the side chains as defined above. These vitamin D starting materials are known compounds, or compounds that can be prepared by known methods.

Using the procedure of DeLuca et al U.S. Pat. No. 4,195,027, the starting material is converted to the corresponding 1α-hydroxy-3,5-cyclovitamin D derivative, having the general structure V below, where $X^3$ represents hydrogen and Q represents an alkyl, preferably methyl:

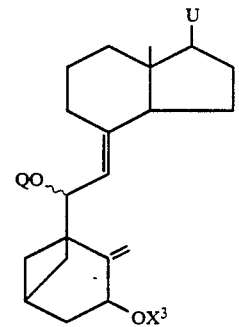

V

So as to preclude undesired reaction of the 1α-hydroxy group in subsequent steps, the hydroxy group is converted to the corresponding acyl derivative, i.e. the compound V shown above, where $X^3$ represents an acyl group, using standard acylation procedures, such as treatment with an acyl anhydride or acyl halide in pyridine at room temperature or slightly elevated temperature (30°–70° C.). It should be understood also that whereas the process of this invention is illustrated here with acyl protection of hydroxy functions, alternative standard hydroxy-protecting groups can also be used, such as, for example, alkylsilyl or alkoxyalkyl groups. Such protecting groups are well-known in the art (e.g. trimethylsilyl, triethylsilyl, t.-butyldimethylsilyl, or tetrahydrofuranyl, methoxymethyl), and their use is considered a routine modification of experimental detail within the scope of the process of this invention.

The derivative as obtained above is then reacted with osmium tetroxide, to produce the 10,19-dihydroxy analog, VI (where $X^3$ is acyl), which is subjected to diol cleavage using sodium metaperiodate or similar vicinal diol cleavage reagents (e.g. lead tetraacetate) to obtain the 10-oxo-intermediate, having the structure VII below (where $X^3$ is acyl):

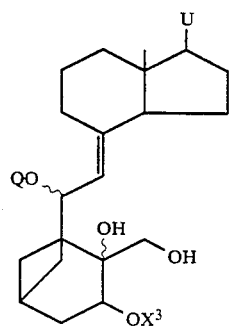

VI

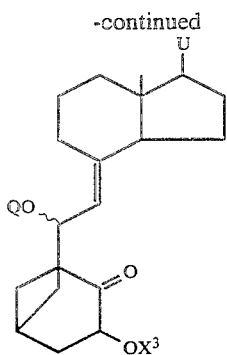

VII

These two consecutive steps can be carried out according to the procedures given by Paaren et al. (J. Org. Chem. 48, 3819 (1983)). If the side chain unit, U carries vicinal diols (e.g. 24,25-dihydroxy- or 25,26-dihydroxy, etc.), these, of course, also need to be protected, e.g. via acylation, silylation, or as the isopropylidene derivative prior to the periodate cleavage reactions.

In most cases, the acylation of the 1α-hydroxy group as mentioned above will simultaneously effect the acylation of side chain hydroxy functions, and these acylation conditions can, of course, be appropriately adjusted (e.g. elevated temperatures, longer reaction times) so as to assure complete protection of side chain vicinal diol groupings.

The next step of the process comprises the reduction of the 10-oxo-group to the corresponding 10-alcohol having the structure VIII shown below (where $X^3$ is acyl and $Y^3$ represents hydroxy). When $X^3$ is acyl, this reduction is carried out conveniently in an organic solvent at from about 0° C. to about room temperature, using $NaBH_4$ or equivalent hydride reducing agents, selective for the reduction of carbonyl groups without cleaving ester functions. Obviously, when $X^3$ is a hydroxy-protecting group that is stable to reducing agents, any of the other hydride reducing agents (e.g. $LiAlH_4$, or analogous reagents) may be employed also.

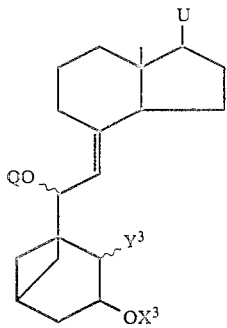

VIII

The 10-hydroxy intermediate is then treated with an alkyl-or arylsulfonylhalide (e.g. methanesulfonylchloride) in a suitable solvent (e.g. pyridine) to obtain the corresponding 10-0-alkyl-or arylsulfonyl derivative (the compound having the structure shown VIII above, where $Y^3$ is alkyl—$SO_2O$—, or aryl—$SO_2O$—, and this sulfonate intermediate is then directly reduced, with lithium aluminum hydride, or the analogous known lithium aluminum alkyl hydride reagents in an ether solvent, at a temperature ranging from 0° C. to the boiling temperature of the solvent, thereby displacing the sulfonate group and obtaining the 10-deoxy derivative, represented by the structure VIII above, where $X^3$ and $Y^3$ are both hydrogen. As shown by the above structure, a 1-0-acyl function in the precursor compound VII is also cleaved in this reduction step to produce the free 1α-hydroxy function, and any 0acyl protecting group in the side chain would, of course, likewise be reduced to the corresponding free alcohol function, as is well understood in the art. If desired, the hydroxy groups at C-1 (or hydroxy groups in the side chain) can be reprotected by acylation or silylation or ether formation to the corresponding acyl, alkylsilyl or alkoxyalkyl derivative, but such protection is not required. Alternative hydroxy-protecting groups, such as alkylsilyl or alkoxyalkyl groups would be retained in this reduction step, but can be removed, as desired, at this or later stages in the process by standard methods known in the art.

The above 1α-hydroxy-10-deoxy cyclovitamin D intermediate is next solvolyzed in the presence of a low-molecular weight organic acid, using the conditions of DeLuca et al U.S. Pat. Nos. 4,195,027 and 4,260,549. When the solvolysis is carried out in acetic acid, for example, there is obtained a mixture of 1α-hydroxy-19-nor-vitamin D 3-acetate and 1α-hydroxy-19-nor-vitamin D 1-acetate (compounds IX and X, below), and the analogous 1- and 3-acylates are produced, when alternative acids are used for solvolysis.

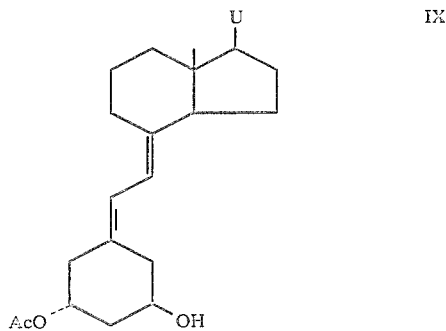

IX

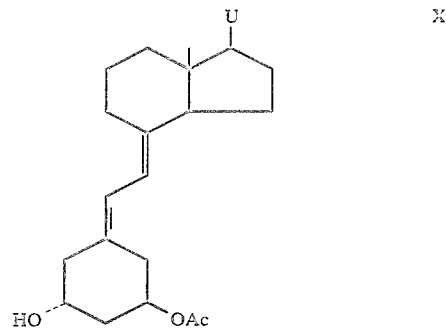

X

Direct basic hydrolysis of this mixture under standard conditions then produces the desired 1α-hydroxy-19-nor-vitamin D compounds of structure II above (where $X^1$ and $Y^1$ are both hydrogen). Alternatively, the above mixture of monoacetates may also be separated (e.g. by high pressure liquid chromatography) and the resulting 1-acetate and 3-acetate isomers may be subjected separately to hydroxysis to obtain the same final product from each, namely the 1α-hydroxy-19-nor-vitamin D compounds of structure II. Also the separated monoacetates of structure IX or X or the free 1,3-dihydroxy compound can, of course, be reacylated according to standard procedures with any desired acyl group, so as to produce the product of structure II above, where $X^1$ and $Y^1$ represent acyl groups which may be the same or different.

The 19-nor-vitamin D compounds useful in this invention are more specifically described by the following illustrative examples. In these examples specific products identified by Roman numerals and letters, i.e. IIa, IIb, ..., etc. refer to the specific structures and side chain combinations identified in the preceding description.

EXAMPLE 1

Preparation of 1α,25-dihydroxy-19-nor-vitamin $D_3$ (IIa)

(a) 1α,25-Dihydroxy-3,5-cyclovitamin D 1-acetate, 6-methyl ether

Using 25-hydroxyvitamin $D_3$ (IVa) as starting material, the known 1α,25-dihydroxy-3,5-cyclovitamin derivative Va ($X^3$=H) was prepared according to published procedures (DeLuca et al., U.S. Pat. No. 4,195,027 and Paaren et al., J. Org. Chem. 45, 3252 (1980)). This product was then acylated under standard conditions to obtain the corresponding 1-acetate derivative Va ($X^3$=Ac).

(b) 10,19-Dihydro-1α,10,19,25-tetrahydroxy-3,5-cyclovitamin $D_3$ 1-acetate, 6-methyl ether (VIa)

Intermediate Va ($X^3$=Ac) was treated with a slight molar excess of osmium tetroxide in pyridine according to the general procedure described by Paaren et al. (J. Org. Chem. 48, 3819 (1983)) to obtain the 10,19-dihydroxylated derivative VIa. Mass spectrum m/z (relative intensity), 506 ($M^+$, 1), 488 (2), 474 (40), 425 (45), 396 (15), 285 (5), 229 (30), 133 (45), 59 (80), 43 (100). $^1$H, NMR (CDCl$_3$) δ 0.52 (3H, s, 18—CH$_3$, 0.58 (1H, m, 3—H), 0.93 (3H, d, J=6.1 Hz, 21—CH$_3$, 1.22 (6H, s, 26—CH$_3$ and 27—CH$_3$), 2.10 (3H, s, COCH$_3$), 3.25 (3H, s, 6—OCH$_3$ 3.63 (2H, m, 19—CH$_2$), 4.60 (1H, d, J=9.2 Hz, 6—H), 4.63 (1H, dd, 1β—H), 4.78 (1H, d, J=9.2 Hz, 7—H).

(c) 1α,25-Dihydroxy-10-oxo-3,5-cyclo-19-nor-vitamin $D_3$ 1-acetate, 6-methyl ether (VIIa)

The 10,19-dihydroxylated intermediate VIa was treated with a solution of sodium metaperiodate according to the procedure given by Paaren et al. (J. Org. Chem. 48, 3819, 1983) to produce the 10-oxo-cyclovitamin D derivative (VIIa, $X^3$=Ac). Mass spectrum m/z (relative intensity) 442 ($M^+$—MeOH) (18), 424 (8), 382 (15), 364 (35), 253 (55), 225 (25), 197 (53), 155 (85), 137 (100). $^1$H NMR (CDCl$_3$) δ 0.58 (3H, s, 18—CH$_3$), 0.93 (3H, d, J=6.6 Hz, 21—CH$_3$), 1.22 (6H, s, 26—CH$_3$ and 27—CH$_3$), 2.15 (s, 3—OCOCH$_3$), 3.30 (3H, s, 6—OCH$_3$), 4.61 (1H, d, J=9.1 Hz, 6—H), 4.71 (1H, d, J=9.6 Hz, 7—H), 5.18 (1H,m, 1β—H).

It has been found also that this diol cleavage reaction does not require elevated temperatures, and it is, indeed, generally preferable to conduct the reaction at approximately room temperature.

(d) 1α-Acetoxy-10,25-dihydroxy-3,5-cyclo-19-nor-vitamin $D_3$ 6-methyl ether (VIIIa, $X^3$=Ac, $Y^3$=OH)

The 10-oxo derivative VIIa ($X^3$=Ac) (2.2 mg, 4.6 μmol) was dissolved in 0.5 ml of ethanol and to this solution 50 μl (5.3 μmol) of a NaBH$_4$ solution (prepared from 20 mg of NaBH$_4$, 4.5 ml water and 0.5 ml of 0.01N NaOH solution) was added and the mixture stirred at 0° C. for ca. 1.5 h, and then kept at 0° C. for 16 h. To the mixture ether was added and the organic phase washed with brine, dried over MgSO$_4$, filtered and evaporated. The crude product was purified by column chromatography on a 15×1 cm silica gel column and the alcohol VIIIa ($X^3$=Ac, $Y^3$=OH) was eluted with ethyl acetate hexane mixtures to give 1.4 mg (3 μmol) of product. Mass spectrum m/z (relative intensity) 476 ($M^+$) (1), 444 (85), 426 (18), 384 (30), 366 (48), 351 (21), 255 (35), 237 (48), 199 (100), 139 (51), 59 (58).

(e) 1α,25-Dihydroxy-19-nor-vitamin $D_3$ (IIa, $X^1$=$Y^1$=H)

The 10-alcohol (VIIIa, $X^3$=Ac, $Y^3$=OH) (1.4 mg) was dissolved in 100 μl anhydrous CH$_2$Cl$_2$ and 10 μl (14 μmol) triethylamine solution (prepared from 12 mg (16 μl) triethylamine in 100 μl anhydrous CH$_2$Cl$_2$), followed by 7 μl (5.6 μmol) methyl chloride solution (9 mg mesyl chloride, 6.1 μl, in 100 μl anhydrous CH$_2$Cl$_2$) added at 0° C. The mixture was stirred at 0° C. for 2 h. The solvents were removed with a stream of argon and the residue (comprising compound VIIIa, $X^3$=Ac, $Y^3$=CH$_3$SO$_2$O—) dissolved in 0.5 ml of anhydrous tetrahydrofuran; 5 mg of LiAlH$_4$ was added at 0° C. and the mixture kept at 0° C. for 16 h. Excess LiAlH$_4$ was decomposed with wet ether, the ether phase was washed with water and dried over MgSO$_4$, filtered and evaporated to give the 19-nor product VIIIa ($X^3$=$Y^3$=H).

This product was dissolved in 0.5 ml of acetic acid and stirred at 55° C. for 20 min. The mixture was cooled, ice water added and extracted with ether. The other phase was washed with cold 10% sodium bicarbonate solution, brine, dried over MgSO$_4$, filtered and evaporated to give the expected mixture of 3-acetoxy-1-α-hydroxy- and 1α-acetoxy-3-hydroxy isomers, which were separated and purified by HPLC (Zorbax Sil column, 6.4×25 cm, 2-propanol in hexane) to give about 70 μg each of compounds IXa and Xa. UV (in EtOH) $λ_{max}$ 242.5 (OD 0.72), 251.5 (OD 0.86), 260 (OD 0.57).

Both 19-nor-1,25-dihydroxyvitamin D$_3$ acetates IXa and Xa were hydrolyzed in the same manner. Each of the monoacetates was dissolved in 0.5 ml of ether and 0.5 ml 0.1N KOH in methanol was added. The mixture was stirred under argon atmosphere for 2 h. More ether was added and the organic phase washed with brine, dried over anhydrous MgSO$_4$, filtered and evaporated. The residue was dissolved in a 1:1 mixture of 2-propanol and hexane and passed through a Sep Pak column and washed with the same solvent. The solvents were evaporated and the residue purified by HPLC (Zorbax Sil, 6.4×25 cm, 10% 2-propanol in hexane). The hydrolysis products of IXa and Xa were identical and gave 66 μg of IIa ($X^1$=$Y^1$=H). Mass spectrum (mz relative intensity) 404 ($M^+$) (100), 386 (41), 371 (20), 275 (53), 245 (51), 180 (43), 135 (72), 133 (72), 95 (82), 59 (18), exact mass calcd. for C$_{26}$H$_{44}$O$_3$ 404.3290, found 404.3272. $^1$H NMR (CDCl$_3$) δ 0.52 (3H, s, 18—CH$_3$), 0.92 (3H, d, J=6.9 Hz, 21—CH$_3$), 1.21(6H, s, 26—CH$_3$ and 27—CH$_3$), 4.02 (1H, m, 3αH), 4.06 (1H, m, 1β—H), 5.83 (1H, d, J=11.6 Hz, 7—H), 6.29 (1H, d, J=10.7Hz, 6—H). UV (in EtOH), $λ_{max}$ 243 (OD 0.725), 251.5 (OD 0.823), 261 (OD 0.598).

EXAMPLE 2

Preparation of 1α-hydroxy-19-nor-vitamin $D_3$ (IIb)

(a) With vitamin $D_3$ (IVb) as starting material, and utilizing the conditions of Example 1a, there is obtained known 1α-hydroxy-3,5-cyclovitamin D$_3$ 1-acetate, 6-methyl ether, compound Vb (X$^3$=Ac).

(b) By subjecting intermediate Vb (X$^3$=Ac), as obtained in Example 2a above to the conditions of Example 1b, there is obtained 10,19-dihydro-1α,10,19-trihydroxy-3,5-cyclovitamin D$_3$ 1-acetate, 6-methyl ether VIb (X$^3$=Ac).

(c) By treatment of intermediate VIb (X$^3$=Ac) with sodium metaperiodate according to Example 1c above, there is obtained 1α-hydroxy-10-oxo-3,5-cyclo-19-nor-vitamin D$_3$ 1-acetate, 6-methyl ether VIIb (X$^3$=Ac).

(d) Upon reduction of the 10-oxo-intermediate VIIb (X$^3$=Ac) under the conditions of Example 1d above, there is obtained 1α-acetoxy-10-hydroxy-3,5-cyclo-19-nor-vitamin D$_3$ 6-methyl ether VIIIb (X$^3$=Ac, Y$^3$=OH).

(e) Upon processing intermediate VIIIb (X$^3$=Ac, Y$^3$=OH) through the procedure given in Example 1e above, there is obtained 1α-hydroxy-19-nor-vitamin D$_3$ (IIb, X$^1$=Y$^1$=H).

EXAMPLE 3

Preparation of 1α-hydroxy-19-nor-vitamin D$_2$ (a) With vitamin D$_2$ (IVd) as starting material, and utilizing the conditions of Example 1a, there is obtained known 1α-hydroxy-3,5-cyclovitamin D$_2$ 1-acetate, 6-methyl ether, compound Vd (X$^3$=Ac).

(b) By subjecting intermediate Vd (X$^3$=Ac), as obtained in Example 4a above to the conditions of Example 1b, there is obtained 10,19-dihydro-1α,10,19-trihydroxy-3,5-cyclovitamin D$_2$ 1-acetate, 6-methyl ether, VId (X$^3$=Ac).

(c) By treatment of intermediate VId (X$^3$=Ac) with sodium metaperiodate according to Example 1c above, there is obtained 1α-hydroxy-10-oxo-3,5-cyclo-19-nor-vitamin D$_2$ 1-acetate, 6-methyl ether, VIId (X$^3$=Ac).

(d) Upon reduction of the 10-oxo-intermediate VIId (X$^3$=Ac) under the conditions of Example 1d above, there is obtained 1α-acetoxy-10-hydroxy-3,5-cyclo-19-nor-vitamin D$_2$ 6-methyl ether, VIIId (X$^3$=Ac, Y$^3$=OH).

(e) Upon processing intermediate VIIId (X$^3$=Ac, Y$^3$=OH) through the procedure given in Example 1e above, there is obtained 1α-hydroxy-19-nor-vitamin D$_2$ (IId, X$^1$=Y$^1$=H).

Compositions for use in the above-mentioned treatment of psoriasis and other malignancies comprise an effective amount of one or more 1α-hydroxy-19-nor-vitamin D compounds as defined by the above formula II as the active ingredient, and a suitable carrier. An effective amount of such compounds for use in accordance with this invention is from about 0.01 μg to about 100 μg per gm of composition, and may be administered topically, orally or parenterally in dosages of from about 0.1 μg/day to about 100 μg/day.

The compounds may be formulated as creams, lotions, ointments, topical patches, pills, capsules or tablets, or in liquid form as solutions, emulsions, dispersions or suspensions in pharmaceutically innocuous and acceptable solvent or oils, and such preparations may contain in addition other pharmaceutically innocuous or beneficial components, such as antioxidants, emulsifiers, coloring agents, binders or coating materials.

The compounds may be administered topically, as oral doses, or parenterally by injection or infusion of suitable sterile solutions. The compounds are advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

Biological Activity of 1α-Hydroxy-19-Nor-Vitamin D Compounds

The 19-nor compounds of this invention exhibit a pattern of biological activity having high potency in promoting the differentiation of malignant cells and little or no activity in calcifying bone tissue. This is illustrated by the biological assay results obtained for 1α,25-dihydroxy-19-nor-vitamin D$_3$ which are summarized in Tables 1 and 2, respectively. As previously noted herein, this 1α,25-dihydroxy-19-nor compound is the metabolite of the 1α-hydroxy-19-nor compound that would fall within the structure of formula II. Table 1 shows a comparison of the activity of the known active metabolite 1α,25-dihydroxyvitamin D$_3$ and the 19-nor analog 1α,25-dihydroxy-19-nor-vitamin D$_3$ in inducing the differentiation of human leukemia cells (HL-60 cells) in culture to normal cells (monocytes). Differentiation activity was assessed by three standard differentiation assays, abbreviated in Table 2 as NBT (nitroblue tetrazolium reduction), NSE (non-specific esterase activity), and PHAGO (phagocytosis activity). The assays were conducted according to known procedures, as given, for example, by DeLuca et al. (U.S. Pat. No. 4,717,721 and Ostrem et al., J. Biol. Chem. 262, 14164, 1987). For each assay, the differentiation activity of the test compounds is expressed in terms of the percent of HL-60 cells having differentiated to normal cells in response to a given concentration of test compound.

The results summarized in Table 1 clearly show that the analog, 1α,25-dihydroxy-19-nor-vitamin D$_3$ is as potent as 1α,25-dihydroxyvitamin D$_3$ in promoting the differentiation of leukemia cells. Thus in all three assays close to 90% of the cells are induced to differentiate by 1α,25-dihydroxy-vitamin D$_3$ at a concentration of $1 \times 10^{-7}$ molar, and the same degree of differentiation (i.e. 90, 84 and 90%) is achieved by the 19-nor analog.

TABLE 1

| Differentiation of HL-60 Cells | | | |
|---|---|---|---|
| | % Differentiated Cells (mean ± SEM) | | |
| | NBT | NSE | PHAGO |
| 1α,25-dihydroxyvitamin D$_3$ (moles/liter) | | | |
| $1 \times 10^{-7}$ | 86 ± 2 | 89 ± 1 | 87 ± 3 |
| $1 \times 10^{-8}$ | 60 ± 2 | 60 ± 3 | 64 ± 2 |
| $1 \times 10^{-9}$ | 33 ± 2 | 31 ± 2 | 34 ± 1 |
| 1α,25-Dihydroxy-19-nor-vitamin D$_3$ (moles/liter) | | | |
| $2 \times 10^{-7}$ | 94 ± 2 | 95 ± 3 | 94 ± 2 |
| $1 \times 10^{-7}$ | 90 ± 4 | 84 ± 4 | 90 ± 4 |
| $5 \times 10^{-8}$ | 72 ± 3 | 73 ± 3 | 74 ± 3 |
| $1 \times 10^{-8}$ | 61 ± 3 | 60 ± 3 | 56 ± 1 |
| $1 \times 10^{-9}$ | 32 ± 1 | 31 ± 1 | 33 ± 1 |

In contrast to the preceding results, the 19-nor analog exhibits no activity in an assay measuring the calcification of bone, a typical response elicited by vitamin D compounds. Relevant data, representing the results of an assay comparing the bone calcification activity in rats of 1α,25-dihydroxyvitamin D$_3$ and 1α,25-dihydroxy-19-nor vitamin D$_3$ are summarized in Table 2.

This assay was conducted according to the procedure described by Tanaka et al., Endocrinology 92, 417 (1973).

The results presented in Table 2 show the expected bone calcification activity of 1α,25-dihydroxyvitamin $D_3$ as reflected by the increase in percent bone ash, and in total ash at all dose levels. In contrast, the 19-nor analog exhibits no activity at all three dose levels, when compared to the vitamin D-deficient (−D) control group.

TABLE 2

| Compound | Amount Administered* (pmoles/day/ 7 days) | % Ash (mean ± SEM) | Total Ash (mg) (mean ± SEM) |
| --- | --- | --- | --- |
| -D (control) | 0 | 19 ± 0.8 | 23 ± 1.2 |
| 1α,25-dihydroxy-vitamin $D_3$ | 32.5 | 23 ± 0.5 | 34 ± 1.6 |
|  | 65.0 | 26 ± 0.7 | 36 ± 1.1 |
|  | 325.0 | 28 ± 0.9 | 40 ± 1.9 |
| 1α,25-dihydroxy-19-nor-vitamin $D_3$ | 32.5 | 22 ± 0.9 | 28 ± 1.6 |
|  | 65.0 | 19 ± 1.5 | 28 ± 3.4 |
|  | 325.0 | 19 ± 1.2 | 30 ± 2.4 |

*Each assay group comprised 6 rats, receiving the indicated amount of test compound by intraperitoneal injection daily for a period of seven days.

Thus the 19-nor analog shows a selective activity profile combining high potency in inducing the differentiation of malignant cells with very low or no bone calcification activity. The compounds of this novel structural class, therefore, can be useful as therapeutic agents for the treatment of psoriasis and other malignancies.

It should be specifically noted that 1α-hydroxy-19-nor-vitamin $D_3$ is expected to be less active than 1α,25-dihydroxy-19-nor-vitamin $D_3$ in causing differentiation of HL60 cells in vitro. However, in vivo it is well established that 1α-hydroxy-19-nor-vitamin $D_3$ is rapidly converted to 1α,25-dihydroxy-19-nor-vitamin $D_3$, Hollick et al, *Science*, Vol. 190, pages 576–578 (1975) and Hollick et al, *Journal of Clinical Endocrinology & Metabolism*, Vol. 44, pages 595–598 (1977), which compound as shown herein is highly potent in cell differentiation. Thus, it is clear that the human body can rapidly convert the relatively inactive 1α-hydroxylated-19-nor-vitamin D compounds to metabolites highly active in causing cell differentiation. This in vivo capability makes possible the treatment of malignancies such as psoriasis with 1α-hydroxylated-19-nor-vitamin D compounds that do not initially have a hydroxyl group at the 24 or 25 carbon position in the side chain.

We claim:

1. A method for treating psoriasis which comprises administering to a patient an effective amount of a compound of the formula:

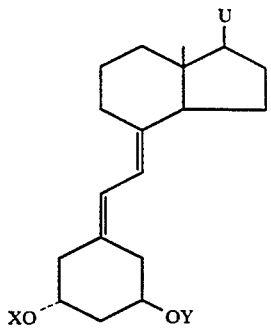

where X and Y are each selected from the group consisting of hydrogen, acyl, alkylsilyl and alkoxyalkyl, and where U is selected from a side chain of the formula

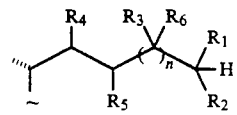

wherein $R_1$ and $R_2$ are each selected from the group consisting of alkyl, deuteroalkyl, hydroxyalkyl and fluoroalkyl, or, when taken together represent the group—$(CH_2)_m$—where m is an integer having a value of from 2 to 5, $R_3$ is selected from the group consisting of hydrogen, deuterium, hydroxy, fluorine, O-acyl, alkyl, hydroxyalkyl and fluoroalkyl, $R_6$ is selected from the group consisting of hydrogen, deuterium, fluorine, alkyl, hydroxyalkyl and fluoroalkyl, or, $R_3$ and $R_6$ taken together represent double-bonded oxygen or double-bonded carbon, $R_4$ and $R_5$ are each selected from the group consisting of hydrogen, deuterium, hydroxy, O-acyl, fluorine and alkyl, or, $R_4$ and $R_5$ taken together form a carbon-carbon double bond or a carbon-carbon triple bond, and wherein n is an integer having a value of from 1 to 5 and wherein the carbon at any one of positions 20, 22, or 23 in the side chain may be replaced by an O, S, or N atom with the proviso that when n is 1 then $R_1$ and $R_2$ must both be methyl.

2. The method of claim 1 wherein said compound is 1α-hydroxy-19-nor-vitamin $D_3$.

3. The method of claim 1 wherein said compound is 1α-hydroxy-19-nor-24,24-difluoro-vitamin $D_3$.

4. The method of claim 1 wherein said compound is 1α-hydroxy-19-nor-26,27-hexadeutero-vitamin $D_3$.

5. The method of claim 1 wherein said compound is 1α-hydroxy-19-nor-26,27-hexafluorovitamin $D_3$.

6. The method of claim 1 wherein said compound is 1α-hydroxy-19-nor-vitamin $D_2$.

7. The method of claim 1 wherein the compound is 24-homo-1α-hydroxy-19-nor-22-dehydrovitamin $D_3$.

8. The method of claim 1 wherein the compound is 24-dihomo-1α-hydroxy-19-nor-22-dehydrovitamin $D_3$.

9. The method of claim 1 wherein the compound is 24-trihomo-1α-hydroxy-19-nor-22-dehydrovitamin $D_3$.

10. The method of claim 1 wherein the compound is 26,27-dimethyl-24-dihomo-1α-hydroxy-19-nor-22-dehydrovitamin $D_3$.

11. The method of claim 1 wherein the compound is 26,27-dimethyl-24-trihomo-1α-hydroxy-19-nor-22-dehydrovitamin $D_3$.

12. The method of claim 1 wherein the compound is 26,27-diethyl-24-dihomo-1α-hydroxy-19-nor-22-dehydrovitamin $D_3$.

13. The method of claim 1 wherein the compound is 26,27-diethyl-24-trihomo-1α-hydroxy-19-nor-22-dehydrovitamin $D_3$.

14. The method of claim 1 wherein the compound is 26,27-dipropyl-24-dihomo-1α-hydroxy-19-nor-22-dehydrovitamin $D_3$.

15. The method of claim 1 wherein the compound is 26,27-dipropyl-24-trihomo-1α-hydroxy-19-nor-22-dehydrovitamin $D_3$.

16. The method of claim 1 wherein the compound is 24-homo-1α-hydroxy-19-nor-vitamin $D_3$.

17. The method of claim 1 wherein the compound is 24-dihomo-1α-hydroxy-19-nor-vitamin $D_3$.

18. The method of claim 1 wherein the compound is 24-trihomo-1α-hydroxy-19-nor-vitamin $D_3$.

19. The method of claim 1 wherein the compound is 26,27-dimethyl-24-dihomo-1α-hydroxy-19-nor-vitamin $D_3$.

20. The method of claim 1 wherein the compound is 26,27-dimethyl-24-trihomo-1α-hydroxy-19-nor-vitamin $D_3$.

21. The method of claim 1 wherein the compound is 26,27-diethyl-24-dihomo-1αhydroxy-19-nor-vitamin $D_3$.

22. The method of claim 1 wherein the compound is 26,27-diethyl-24-trihomo-1α-hydroxy-19-nor-vitamin $D_3$.

23. The method of claim 1 wherein the compound is 26,27-dipropyl-24-dihomo-1α-hydroxy-19-nor-vitamin $D_3$.

24. The method of claim 1 wherein the compound is 26,27-dipropyl-24-trihomo-1α-hydroxy-19-nor-vitamin $D_3$.

25. The method of claim 1 wherein the compound is 1α-hydroxy-19-nor-24 epi-vitamin $D_2$.

26. The method of claim 1 wherein said effective amount comprises about 0.01 μg/day to about 100 μg/day of said compound.

27. A composition for use in the treatment of psoriasis which comprises an effective amount of a compound of the formula:

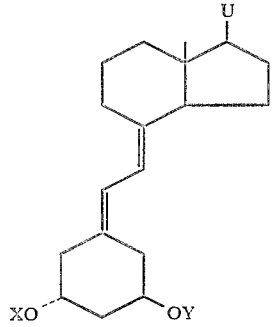

where X and Y are each selected from the group consisting of hydrogen, acyl, alkylsilyl and alkoxyalkyl, and where U is selected from a side chain of the formula

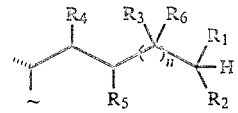

wherein $R_1$ and $R_2$ are each selected from the group consisting of alkyl, deuteroalkyl, hydroxyalkyl and fluoroalkyl, or, when taken together represent the group—$(CH_2)_m$—where m is an integer having a value of from 2 to 5, $R_3$ is selected from the group consisting of hydrogen, deuterium, hydroxy, fluorine, O-acyl, alkyl, hydroxyalkyl and fluoroalkyl, $R_6$ is selected from the group consisting of hydrogen, deuterium, fluorine, alkyl, hydroxyalkyl and fluoroalkyl, or, $R_3$ and $R_6$ taken together represent double-bonded oxygen or double-bonded carbon, $R_4$ and $R_5$ are each selected from the group consisting of hydrogen, deuterium, hydroxy, O-acyl, fluorine and alkyl, or, $R_4$ and $R_5$ taken together form a carbon-carbon double bond or a carbon-carbon triple bond, and wherein n is an integer having a value of from 1 to 5 and wherein the carbon at any one of positions 20, 22, or 23 in the side chain may be replaced by an O, S, or N atom with the proviso that when n is 1 then $R_1$ and $R_2$ must both be methyl.

28. The composition of claim 27 wherein said compound is 1α-hydroxy-19-nor-vitamin $D_3$.

29. The composition of claim 27 wherein said compound is 1α-hydroxy-19-nor-24,24-difluoro-vitamin $D_3$.

30. The composition of claim 27 wherein said compound is 1α-hydroxy-19-nor-26,27-hexadeutero-vitamin $D_3$.

31. The composition of claim 27 wherein said compound is 1α-hydroxy-19-nor-26,27-hexafluorovitamin $D_3$.

32. The composition of claim 27 wherein said compound is 1α-hydroxy-19-nor-vitamin $D_2$.

33. The composition of claim 27 wherein the compound is 24-homo-1α-hydroxy-19-nor-22-dehydrovitamin $D_3$.

34. The composition of claim 27 wherein the compound is 24-dihomo-1α-hydroxy-19-nor-22-dehydrovitamin $D_3$.

35. The composition of claim 27 wherein the compound is 24-trihomo-1α-hydroxy-19-nor-22dehydrovitamin $D_3$.

36. The composition of claim 27 wherein the compound is 26,27-dimethyl-24-dihomo-1α-hydroxy-19-nor-22-dehydrovitamin $D_3$.

37. The composition of claim 27 wherein the compound is 26,27-dimethyl-24-trihomo-1α-hydroxy-19-nor-22-dehydrovitamin $D_3$.

38. The composition of claim 27 wherein the compound is 26,27-diethyl-24-dihomo-1α-hydroxy-19-nor-22-dehydrovitamin $D_3$.

39. The composition of claim 27 wherein the compound is 26,27-diethyl-24-trihomo-1α-hydroxy-19-nor-22-dehydrovitamin $D_3$.

40. The composition of claim 27 wherein the compound is 26,27-dipropyl-24-dihomo-1α-hydroxy-19-nor22-dehydrovitamin $D_3$.

41. The composition of claim 27 wherein the compound is 26,27-dipropyl-24-trihomo-1α-hydroxy-19-nor22-dehydrovitamin $D_3$.

42. The composition of claim 27 wherein the compound is 24-homo-1α-hydroxy-19-nor-vitamin $D_3$.

43. The composition of claim 27 wherein the compound is 24-dihomo-1α-hydroxy-19-nor-vitamin $D_3$.

44. The composition of claim 27 wherein the compound is 24-trihomo-1α-hydroxy-19-nor-vitamin $D_3$.

45. The composition to claim 27 wherein the compound is 26,27-dimethyl-24-dihomo-1α-hydroxy-19-nor-vitamin $D_3$.

46. The composition of claim 27 wherein the compound is 26,27-dimethyl-24-trihomo-1α-hydroxy-19-nor-vitamin $D_3$.

47. The composition of claim 27 wherein the compound is 26,27-diethyl-24-dihomo-1α-hydroxy-19-nor-vitamin $D_3$.

48. The composition of claim 27 wherein the compound is 26,27-diethyl-24-trihomo-1α-hydroxy-19-nor-vitamin $D_3$.

49. The composition of claim 27 wherein the compound is 26,27-dipropyl-24-dihomo-1α-hydroxy-19-nor-vitamin $D_3$.

50. The composition of claim 27 wherein the compound is 26,27-dipropyl-24-trihomo-1α-hydroxy-19-nor-vitamin $D_3$.

51. The composition of claim 27 wherein the compound is 1α-hydroxy-19-nor-24 epi-vitamin $D_2$.

52. The composition of claim 27 wherein said effective amount is between about 0.01 μg to about 100 μg per gram of the composition.

53. A method of treating psoriasis which comprises administering to a patient an effective amount of 1α-hydroxylated-19-nor-vitamin D compound which compound upon administering to humans is converted to a metabolite and said metabolite in vitro will cause differentiation of promelocytes to monocytes in a cell line selected from a group consisting of a U937 cell line, an HL60 cell line and a M1 cell line.

* * * * *

UNITED STATES PATENT AND TRADEMARK OFFICE
CERTIFICATE OF CORRECTION

PATENT NO. : 5,321,018
DATED : June 14, 1994
INVENTOR(S) : Hector F. DeLuca

It is certified that error appears in the above-indentified patent and that said Letters Patent is hereby corrected as shown below:

CLAIM 21
Col. 15, line 29
(Original claim 21, line 2)

Delete "1αhydroxy" and substitute therefore ---1α-hydroxy---

CLAIM 35
Col. 16, line 47
(Original claim 35, line 2)

Delete "22dehy-" and substitute therefore ---22-dehy- ---

CLAIM 40
Col. 16, line 63
(Original claim 40, line 2

Delete "nor22" and substitute therefore ---nor-22---

CLAIM 41
Col. 16, line 66
(Original claim 41, line 3)

Delete "nor22" and substitute therefore ---nor-22---

Signed and Sealed this

Twenty-third Day of May, 1995

Attest:

BRUCE LEHMAN

*Attesting Officer*     *Commissioner of Patents and Trademarks*